United States Patent [19]

Smith

[11] 4,182,342

[45] Jan. 8, 1980

[54] NASO-GASTRIC FEEDING DEVICE AND METHOD OF INSERTING SAME

[75] Inventor: Gordon E. Smith, Sun Prairie, Wis.

[73] Assignee: Med-Pro, Ltd., Sun Prairie, Wis.

[21] Appl. No.: 900,914

[22] Filed: Apr. 28, 1978

[51] Int. Cl.² ............................................ A61M 25/00
[52] U.S. Cl. .................................. 128/348; 128/222; 128/DIG. 9
[58] Field of Search ............ 128/213, 214.4, 221–222, 128/348–349 R, 350 R, 350 V, DIG. 9; 221/64, 278; 226/97

[56] References Cited

U.S. PATENT DOCUMENTS

| | | | |
|---|---|---|---|
| 788,176 | 4/1905 | Traves | 128/231 |
| 3,189,031 | 6/1965 | Andersen | 128/350 R |
| 3,228,894 | 1/1966 | Jeckel | 128/349 R |
| 3,460,975 | 8/1969 | Stebelton | 128/348 |
| 3,683,928 | 8/1972 | Kuntz | 128/349 R |
| 3,703,174 | 11/1972 | Smith | 128/214.4 |
| 3,780,740 | 12/1973 | Rhea | 128/350 R |
| 3,826,256 | 7/1974 | Smith | 128/214.4 |
| 3,888,249 | 6/1975 | Spencer | 128/350 V |

*Primary Examiner*—Robert W. Michell
*Assistant Examiner*—C. F. Rosenbaum
*Attorney, Agent, or Firm*—Theodore J. Long; Harry C. Engstrom; Nicholas J. Seay

[57] ABSTRACT

A naso-gastric feeding device is disclosed which includes a highly flexible feeding tube carried inside of a semi-flexible guide tube. The guide tube is inserted into the patient and then fluid is forced through the guide tube into the patient carrying with it the feeding tube. The guide tube is then withdrawn so that only the feeding tube is left in the patient with feeding taking place therethrough.

21 Claims, 6 Drawing Figures

NASO-GASTRIC FEEDING DEVICE AND METHOD OF INSERTING SAME

BACKGROUND OF THE INVENTION

1. Field of the Invention

The present invention relates to devices to feed patients who are unable to or who may not eat and in particular to feeding devices for insertion through the nasal passage and into the gastric tract of a patient.

2. Description of the Prior Art

The prior art is generally cognizant of semi-flexible relatively large diameter tubes of PVC material which are insertable through the nasal passage and into the gastric tract of a patient. It is a problem with such tubes that they are very intrusive and uncomfortable to the patient. The prior art is also cognizant of devices for injecting highly flexible silicone tubing into blood vessels using a liquid to carry the tubing, as exemplified by U.S. Pat. Nos. 3,703,174 and 3,826,256. Such devices are not directly usable for naso-gastric feeding due to the difficulty of feeding the tubing through the nasal passage and pharynx into the gastric tract.

SUMMARY OF THE INVENTION

The present invention is summarized in that a naso-gastric feeding device includes a guide tube of clear semi-flexible material having a distal and a proximal end, a narrowed retaining ring formed inside of the guide tube near the distal end thereof, fluid pressure generating means connected to the proximal end of the guide tube for forcing fluids therethrough, a feeding tube of highly flexible material received within the guide tube and having a distal end and a proximal end, the distal end having a slit formed in its wall surface, an elongated portion of the feeding tube formed at its proximal end, and an anchor attached to the distal end of the feeding tube, the anchor being formed of flexible material having a metallic component included therein, the anchor being initially secured on the distal end of the guide tube.

It is an object of the present invention to provide a method and apparatus for insertion of a highly flexible and relatively inobtrusive feeding tube into a patient to reduce the patient's discomfort during naso-gastric feeding.

It is another object of the present invention to provide such an apparatus in which the placement of the end of the feeding tube can be verified by X-ray examination.

It is yet another object of the present invention to provide such a method and apparatus that operates quickly and efficiently with a minimum of discomfort to the patient.

Other objects, advantages and features of the present invention will become apparent from the following specification when taken in conjunction with the accompanying drawings.

DESCRIPTION OF THE PREFERRED EMBODIMENT

Figure 1:
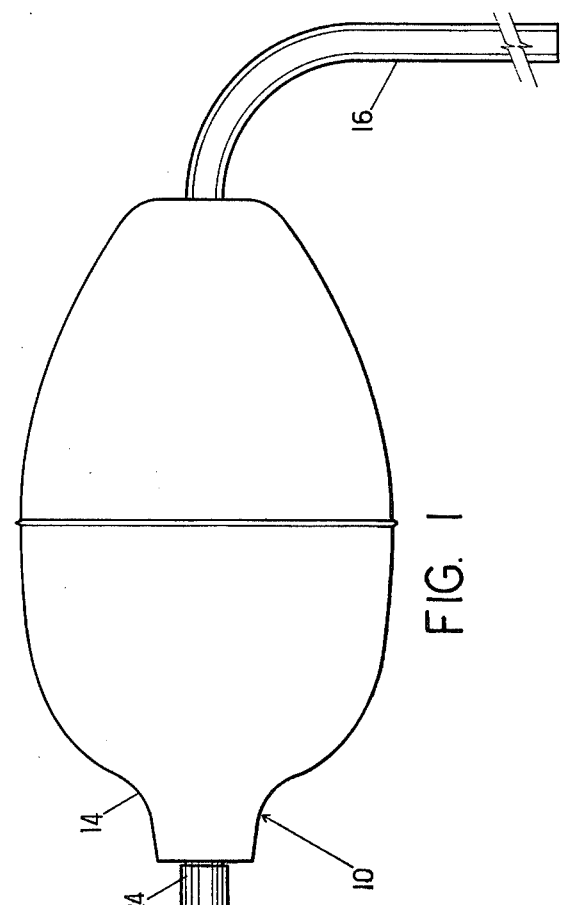
FIG. 1 is a side elevation view of a naso-gastric feeding device constructed according to the present invention.

As is shown in FIG. 1, the present invention is embodied in a naso-gastric feeding device, generally indicated at 10. The feeding device 10 includes an outer guide tube 12 connecting to one end of a bulb 14, an auxiliary tube 16 connecting to the other end of the bulb 14, and an inner feeding tube 18 which is received partially within the guide tube 12 and partially within the bulb 14.

The guide tube 12 is formed of any suitable clear semi-flexible biologically inert material, such as clear poly-vinyl chloride (PVC) tubing. The tubing for the guide tube 12 must be, as stated, semi-flexible, meaning that this tubing must be rigid enough to maintain its internal shape and full interior diameter without pinching under moderate bending yet flexible enough to allow the tubing to be hand-fed through a curved passageway, such as a human naso-gastric passage. At its proximal end, to the right in FIG. 1, the guide tube 12 is attached to a fitting 20 to which a connecting tube 22 is also attached. The connecting tube 22, which is formed of the same material as the guide tube 12, is connected at its other end by a fitting 24 to the bulb 14 to allow free fluid communication between the interiors of the guide tube 12 and the bulb 14. Near the distal end of the guide tube 12, at about 1 to 2 inches from its extreme end, a narrowed annular retaining ring 26 is formed within the interior of the guide tube 12. From end to end the guide tube 12 is preferably approximately 30 inches in length although tubes of different length may be desirable for patients of extremely large or small size.

The bulb 14 is a hollow compressible bulb of flexible rubber or plastic which has its interior connected at one end in uninterrupted fluid communication with the interior of the guide tube 12 by way of the connecting tube 22. The other end of the bulb 14 has included in it a check valve 28 connecting the interior of the bulb 14 with the interior of the auxiliary tube 16. The check valve 28 which is formed by two flexible flaps of material overlapping the inlet of the auxiliary tube 16 into the bulb 14, allows fluid flow from the auxiliary tube 16 into the bulb 14 but inhibits flow in the opposite direction.

Figure 2:
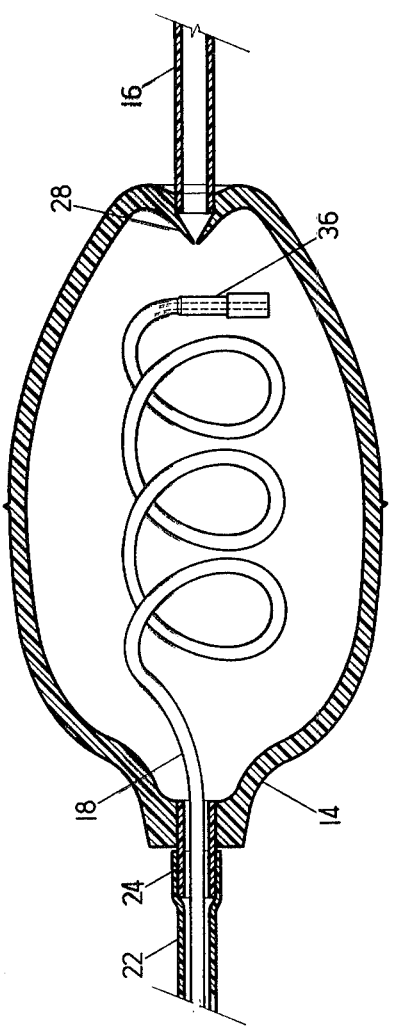
FIG. 2 is a cross-sectional view of the bulb of the feeding device of FIG. 1.

The feeding tube 18 is a thin tube formed of a silicone elastomer or other highly flexible and also biologically inert substance. The tubing for the feeding tube 18 must be highly flexible, meaning that it must be relatively soft and limp to such an extent that the tubing will tend to collapse closed and lose its internal shape when a partial vacuum is applied to its interior. The material forming the feeding tube 18 is opaque so that it may readily be distinguished from the guide tube 12 which surrounds it. At its distal end the feeding tube 18 is secured to an anchor 30 which acts as a closure to close the end of the feeding tube 18, and which rests partially inside the distal end of the guide tube 12. The anchor 30 is a molded member of silicone formed with a metallic component included therein and is tapered larger in size toward its extreme distal end, the anchor 30 being initially wedged in the end of the guide tube 12 so that the end is sealed. The metallic component of the anchor 30 is provided by a mass of powdered metal, such as iron or tungsten, which is incorporated into the silicone from which the anchor 30 is molded. Because of the encapsulating tendency of silicone materials, the silicone for the anchor 30 may contain up to 70 to 90 percent metal by weight and yet will still retain the texture, appearance and feel of silicone alone. The anchor 30 also has formed around its circumference a skirt 32 which is formed to be open in the direction away from the distal end of the anchor 30. A feeding slit 34 is provided in the feeding tube 18 near its distal end and is formed by a simple cut or slice in the wall of the feeding tube 18. At its proximal end the feeding tube 18 is provided with an enlarged portion 36 which is a section of the silicone tubing having thickened wall construction around an interior opening of the same size as the rest of the tube, with the enlarged portion 36 being designed to have an outer diameter slightly greater than the inner diameter of the retaining ring 26 of the guide tube 12. The feeding tube 18 is constructed to be somewhat longer than the guide tube 12, preferably having a total length of about 40 inches. As the feeding device 10 is received by the physician, the proximal end section of the feeding tube 18 is arranged in a coiled fashion in the interior of the bulb 14, as can be seen in FIG. 2. A powdered lubricating material is applied to the exterior of the feeding tube 18 throughout its length to ensure that the feeding tube 18 does not become adhered to the inside of the guide tube 12 at any point. Since such a material must be nontoxic and suitable for introduction into the digestive tract, powdered cornstarch is considered the preferable lubricant.

Figure 4:
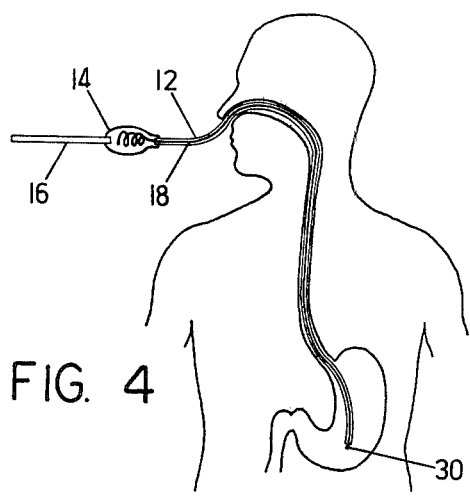
FIG. 4 is a schematic illustration of a first step in the insertion of the feeding device of FIG. 1.
Figure 5:
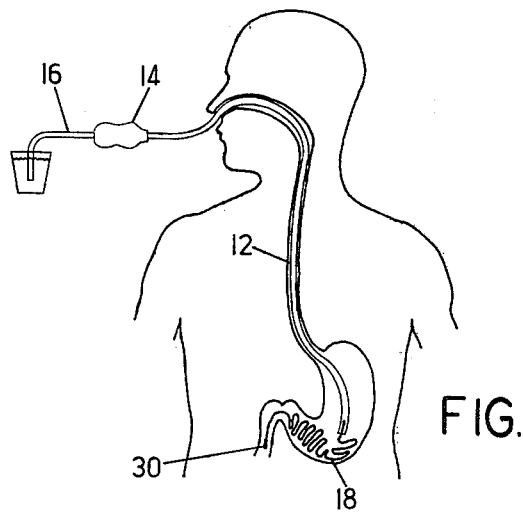
FIG. 5 is a schematic illustration of a subsequent step in the insertion of the feeding device of FIG. 1.

In its operation, the feeding device 10 is intended to serve as a conduit to introduce fluid nutrient material directly into the intestinal tract of a patient. The distal end of the guide tube 12, with the anchor 30 leading, is inserted into the patient's nostril, through his nasal cavity and over the soft palate to the pharynx. A lubricant may be applied to the exterior of the guide tube 12 to aid its passage through these areas, if it is needed. Preferably with the aid of the patient's swallowing, the guide tube 12 is then progressively fed into the patient's nostril so that its distal end travels down the patient's esophagus to his stomach. The position of the end of the guide tube 12 can be checked, if required, by an X-ray which will reveal the precise location of the metallic component included within the anchor 30. This positioning of the guide tube 12 is shown schematically in FIG. 4.

Once the guide tube 12 is so positioned the bulb 14 is compressed, forcing air down the guide tube 12 to force the anchor 30 out of the end of the guide tube 12 so that it hangs freely inside the stomach of the patient. The positioning of the distal end of the guide tube 12 can be roughly checked by additional compression of the bulb 14 forcing air down the guide tube 12 causing a resultant gurgling sound inside the patient. Then with the bulb 14 fully depressed, the free end of the auxiliary tube 16 is placed in water or a weak aqueous solution, and the bulb 14 is released drawing water into the bulb 14. Further compression of the bulb 14 then causes the liquid to flow under pressure down the guide tube 12.

Figure 3:
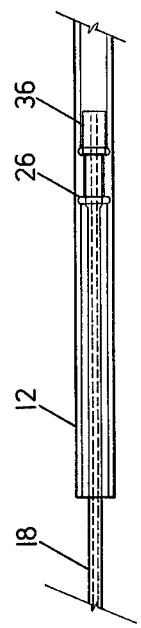
FIG. 3 is a side elevation view of the distal end of the guide tube of the feeding device of FIG. 1 after the feeding tube has been expelled therefrom.

The liquid flows relatively slowly down the guide tube 12 except in the area of the retaining ring 26 where the narrowed fluid passage between the guide tube 12 and the feeding tube 18 causes the liquid to accelerate rapidly through that passage with great velocity. This rapid flow of the liquid inside of the retaining ring 26 exerts a strong frictional force on the feeding tube 18 to pull the feeding tube 18 through the retaining ring 26 and out of the guide tube 18. This rapid flow effect is described in more detail in U.S. Pat. No. 3,703,174 by the inventor of the present invention, the disclosure of this patent being incorporated herein by reference. As the feeding tube 18 is nearly completely exited from the guide tube 12, the force of the liquid then causes the enlarged portion 36 at the proximal end of the feeding tube 18 to be forced into the retaining ring 26 inside the end of the guide tube 12. The forcing of the enlarged portion 36 into the retaining ring 26 forms, as can be seen in FIG. 3, a fluid tight connection between the guide tube 12 and the feeding tube 18. The bulb 14 thus serves as a fluid pressure generating device to generate the fluid flow to carry the feeding tube 18 out of the guide tube 12.

Figure 6:
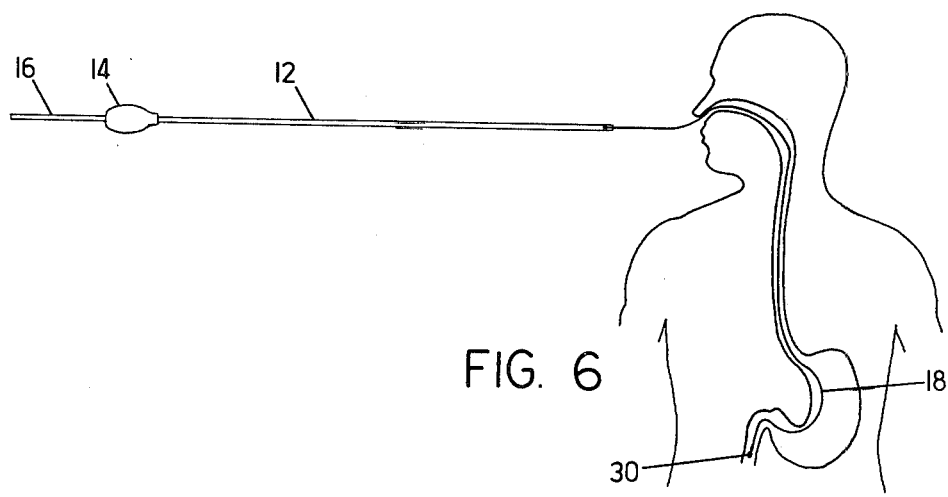
FIG. 6 is a schematic illustration of yet another subsequent step in the insertion of the feeding device of FIG. 1.

The guide tube 12 is then slowly withdrawn from the patient, trailing the feeding tube 18 behind it. The guide tube 12 is completely withdrawn from the patient together with the first few inches of the feeding tube 18, as is shown schematically in FIG. 6. Because of the clear nature of the guide tube 12, the positioning of the feeding tube 18 can be checked as the guide tube 12 is withdrawn to ensure that the feeding tube 18 is completely ejected from the guide tube 12. The distal end of the guide tube 12 can then be secured in place, such as by taping to the side of the patient's head, to keep it out of the patient's way. The bulb 14 is then detached from the guide tube 12 and the proximal end of the guide tube 12 is attached to the nutrient supply. Feeding of the patient then begins as the nutrient travels progressively through the guide tube 12 and then the feeding tube 18 to pass through the feeding slit 34 into the patient's stomach or intestine.

The flexibility of the feeding tube 18 is of great importance in the functioning of the feeding device 10. Since the silicone material is relatively limp and since it is so thin, the feeding tube 18 is relatively inobtrusive to the patient, once installed, and can be left in the patient for extended periods of time, in most cases for many days or even several weeks, without great discomfort. Furthermore, the flexible nature of the feeding tube 18 together with the feeding slit 34 helps to prevent the reverse flow of any of the nutrient or any of the patient's digestive juices in the wrong direction up the feeding tube 18. Should a mishandling of the nutrient supply attached to the guide tube 12 cause a negative pressure to be imposed inside the guide tube 12, the feeding slit 34 will close and the feeding tube 18 collapse to prevent fluid flow in the undesired direction.

The anchor 30 is also of a significant advantage over the prior art. It is relatively small, causing little or no discomfort to the patient, but can readily be located by X-ray scan because of its metallic content. The anchor 30 may alternatively be made of any other dense, nontoxic material which is readily detected by X-ray. If iron powder is used in the anchor 30, the anchor can be detected by magnetic means, though tungsten powder may also be used for maximum weight. The skirt 32 functions to ensure that the anchor 30 is carried downward through the digestive tract by the normal flow of gastric juices so that the feeding tube 18 is extended to its full length. When in place, the skirt 32 also resists upward movement of the anchor 30 thus keeping the anchor 30 in place.

It is also envisioned that the anchor 30 may be formed slightly differently and secured on the end of the guide tube 12 in other ways. For instance, the anchor 30 could be formed in a generally cupped shape which could then be received over the exterior of the end of the guide tube 12. In such a case the feeding tube 18 would preferably be attached to the anchor by threading the feeding tube 18 into and through the material of the anchor 30 with the feeding tube 18 being closed by the resilient pinching action of the silicone in the anchor 30.

The coiling of the excess length of the feeding tube 18 inside of the bulb 14 also allows the feeding tube 18 to be constructed to be any desirable length, regardless of the length of the guide tube 12. Thus, although the relatively large guide tube 12 is inserted only into the stomach, by varying the length of the feeding tube 18, the feeding slit 34 can be placed in the stomach, duodenum or jejunum as desired. The use of the cornstarch lubricant ensures that whatever the length of the feeding tube 18, it will be entirely deposited in the stomach when carried out of the guide tube 12 by the liquid flow.

As mentioned briefly above, the provision for the feeding slit 34 in the highly flexible feeding tube 18 functions as a simple and economical check valve to prevent fluid flow in an undesired direction. Should the fluid pressure outside of the tube 18 adjacent the slit 34 exceed the pressure inside of the tube 18, the tube 18 in the area of the slit 34 would collapse causing the side walls of the slit 34 to come together preventing fluid flow therethrough. Only if a positive pressure gradient from the inside to the outside of the tube 18 is maintained will the sides of the slit 34 open to allow fluid flow therethrough in an outward direction. Thus, a one-way check valve is created in an efficient and economical manner without the need for additional parts.

It is understood that my invention is not limited to the particular construction and arrangement of parts disclosed and illustrated herein, but embraces all modified forms thereof as come within the scope of the following claims.

I claim:

1. A naso-gastric feeding device comprising:
   (a) a guide tube of semi-flexible material having a distal and a proximal end, the guide tube being adapted to be inserted through the nostril and into the stomach of a patient with the proximal end remaining outside the patient;
   (b) a retainer formed inside of the guide tube near the distal end thereof;
   (c) fluid pressure generating means connected to the proximal end of the guide tube for forcing fluids therethrough;
   (d) a feeding tube of highly flexible material received within the guide tube and having a distal and a proximal end, the distal end having a feeding opening formed in its wall surface;
   (e) an enlarged portion of the feeding tube formed at its proximal end; and
   (f) an anchor attached to the distal end of the feeding tube, the anchor being formed of flexible material having a metallic component included therein, the anchor being initially secured on the distal end of the guide tube and being removable therefrom while positioned within the patient by air forced through the guide tube by the fluid pressure generating means;
   (g) the feeding tube being removable from the guide tube into the stomach and intestinal track by liquid forced through the retainer and distal end of the guide tube by the fluid generating means until the feeding tube enlarged portion engages the retainer and is retained thereby within the guide tube, the proximal end of the feeding tube being removable from the patient by withdrawal of the guide tube with the distal end of the feeding tube remaining in the intestinal tract of the patient to deliver nutrients thereto.

2. A naso-gastric feeding device as claimed in claim 1 wherein the anchor includes a distal end and a circumferential skirt oriented in direction away from the distal end of the anchor.

3. A naso-gastric feeding device as claimed in claim 1 wherein the fluid pressure generating means includes a compressible bulb and an auxiliary tube attached to the bulb.

4. A naso-gastric feeding device as claimed in claim 1 wherein the interior of the guide tube is lubricated with a powdered lubricant to aid in the ejection of the feeding tube from the guide tube.

5. A naso-gastric feeding device as claimed in claim 4 wherein the powdered lubricant is cornstarch.

6. A naso-gastric feeding device as claimed in claim 1 wherein the guide tube is formed of polyvinyl chloride.

7. A naso-gastric feeding device as claimed in claim 1 wherein the feeding tube is formed of a silicone elastomer.

8. A naso-gastric feeding device as claimed in claim 1 wherein the retainer is a narrowed annular ring formed on the inside of the guide tube.

9. A naso-gastric feeding device as claimed in claim 1 wherein the feeding opening is formed as a slit in the wall of the highly flexible feeding tube, the feeding tube being collapsible and the slit closeable in response to negative pressure imposed within the feeding tube so as to function as a one-way check valve for fluid flow.

10. A naso-gastric feeding device comprising:
    (a) a guide tube of semi-flexible material having a distal and a proximal end and having a narrowed fluid passage near its distal end, the guide tube being adapted to be inserted through the nostril and into the stomach of a patient with the proximal end remaining outside the patient;
    (b) a compressible bulb attached to the proximal end of the guide tube for forcing fluids therethrough;
    (c) a feeding tube of highly flexible material having a distal and a proximal end and a feeding outlet near the distal end;
    (d) retaining means formed on the feeding tube to prevent the proximal end of the feeding tube from passing through the distal end of the guide tube;
    (e) the feeding tube being longer than the guide tube, with the feeding tube being entirely received within the guide tube for the complete length of the guide tube and with the remaining length of the feeding tube being received within the bulb; and
    (f) a closure secured to the distal end of the feeding tube and being secured within the end of the guide tube, the closure being removable from the guide tube while positioned within the patient by air forced through the guide tube by compression of the bulb;

(g) the feeding tube being removable from the guide tube and bulb into the stomach and intestinal tract by liquid forced through the distal end of the guide tube between the outside of the feeding tube and the inside of the guide tube narrowed fluid passage by compression of the bulb until the feeding tube retaining means is retained at the guide tube narrowed fluid passage, the proximal end of the feeding tube being removable from the patient by withdrawal of the guide tube with the distal end of the feeding tube remaining in the intestinal tract of the patient to deliver nutrients thereto through the outlet.

11. A naso-gastric feeding device as claimed in claim 10 wherein the guide tube is approximately 30 inches in length and the feeding tube is approximately 40 inches in length.

12. A naso-gastric feeding device as claimed in claim 10 wherein the retaining means includes a retaining ring formed inside of the guide tube adjacent its distal end and an enlarged portion formed on the feeding tube at its proximal end.

13. A naso-gastric feeding device as claimed in claim 10 wherein there is an auxiliary tube also connected to the bulb and wherein a check valve is provided in the bulb at its connection with the auxiliary tube so that fluid communication between the bulb and the auxiliary tube is inhibited in one direction.

14. A naso-gastric feeding device as claimed in claim 10 wherein the closure secured to the distal end of the feeding tube is a weighted anchor.

15. A naso-gastric feeding device as claimed in claim 14 wherein the anchor is formed of silicone having a metallic component included therein.

16. A naso-gastric feeding device as claimed in claim 15 wherein the metallic component is iron powder.

17. A naso-gastric feeding device as claimed in claim 15 wherein the metallic component is tungsten powder.

18. A naso-gastric feeding device as claimed in claim 14 wherein the anchor is tapered downward in size away from its distal end and wherein the anchor is initially wedged into the distal end of the guide tube.

19. A method of inserting a highly flexible naso-gastric feeding tube into a patient comprising the steps of:
(a) inserting a semi-flexible guide tube carrying a highly flexible feeding tube therein into the nostrils of the patient and therethrough into the patient's intestinal tract;
(b) forcing air into the guide tube to dislodge an anchor secured on the end of the guide tube, the anchor being attached to the feeding tube, and forcing a liquid through the guide tube and through a narrowed passage therein to carry all but the proximal end of the feeding tube out of the guide tube into the patient; and
(c) drawing the guide tube out of the patient, the guide tube drawing with it the proximal end of the feeding tube so that the feeding tube may be used to introduce nutrients directly into the patient's intestinal tract.

20. A method of inserting a highly flexible naso-gastric feeding tube into a patient as claimed in claim 19 wherein the interior of the guide tube is lubricated with a powdered lubricant to aid in the ejection of the feeding tube from the guide tube.

21. A naso-gastric feeding device as claimed in claim 10 wherein the feeding outlet is a slit in the highly flexible feeding tube, the slit being closeable and the feeding tube being collapsible in response to a negative pressure within the feeding tube to function as a one-way check valve to permit fluid flow from the interior to the exterior of the tube and prevent fluid flow from the exterior to the interior of the tube in response to negative pressure in the tube.

* * * * *